United States Patent [19]
Crooker et al.

[11] Patent Number: 5,169,996
[45] Date of Patent: Dec. 8, 1992

[54] STABILIZED 141B

[75] Inventors: Richard M. Crooker, Lehigh; Maher Y. Elsheikh, Tredyffrin; Robert B. Hager, Collegeville, all of Pa.

[73] Assignee: Elf Atochem North America, Inc., Philadelphia, Pa.

[21] Appl. No.: 773,479

[22] Filed: Oct. 9, 1991

[51] Int. Cl.⁵ .................. C07C 17/42; C07C 19/02
[52] U.S. Cl. .................. 570/111; 252/182.2; 252/182.24; 570/117
[58] Field of Search ................ 570/111, 117

[56] References Cited

FOREIGN PATENT DOCUMENTS

| 95903 | 8/1978 | Japan | 570/111 |
| 49323 | 3/1983 | Japan | 570/111 |
| 825853 | 12/1959 | United Kingdom | 570/119 |

Primary Examiner—Joseph E. Evans

[57] ABSTRACT

HCFC blowing agents such as 141b which are stabilized with diethylhydroxylamine, 1,4-benzoquinone, or 2,6-di-t-butylbenzoquinone.

3 Claims, No Drawings

STABILIZED 141B

FIELD OF THE INVENTION

This invention relates to novel compositions of hydrochlorofluorocarbon ("HCFC") blowing agents such as 1,1-dichloro-1-fluoroethane ("141b") and stabilizing additives (or inhibitors) such as diethylhydroxylamine ("DEHA"), more particularly to compositions of HCFC blowing agents which are stabilized against decomposition in polyol premix formulations or the corresponding polyurethane or polyisocyanurate foams made therefrom.

BACKGROUND OF THE INVENTION

Polyurethane and polyisocyanurate foams are conventionally prepared by reacting an organic polyisocyanate (including diisocyanate) "A-side" component with a "B-side" polyol premix component containing organic polyol, blowing agent, surfactant, catalyst, and possibly other additives such as flame retardants, antioxidants, and U.V. stabilizers. These A-side and B-side components may be purchased by the end-user in separate containers and stored for later use. Since decomposition of the HCFC blowing agents has been observed in the B-side premixes during storage and during the process of making the foam, HCFC compositions inhibited against such decompositions would be highly desirable. For example, the preferred 141b blowing agent has been observed to decompose during the foam-making process to up to about 1%, depending on the formulation and reaction conditions, of various decomposition products of which by far the predominant product is 1-chloro-1-fluoroethylene ("1131a"). Inhibition of such decomposition is desired both because of toxicity concerns and because the decomposition is accompanied by the formation of equivalent amounts of acid which in turn causes catalyst deactivation.

Applicant is not aware of prior disclosures of the herein claimed formulations.

SUMMARY OF THE INVENTION

A composition is provided containing an HCFC blowing agent such as 141b and an inhibitor selected from DEHA, 1,4-benzoquinone, and 2,6-di-t-butylbenzoquinone, preferably DEHA. When incorporated in a premix, the composition may also contain a polyol and, optionally, other ingredients such as surfactants, catalysts, and flame retardants.

DETAILED DESCRIPTION OF THE INVENTION

It has now been found that HCFC blowing agents such as 141b are stabilized against decomposition by the addition of an inhibitor selected from 1,4-benzoquinone, 2,6-di-t-butylbenzoquinone, or, preferably, DEHA.

While the examples illustrate the invention with the preferred 141b blowing agent, the invention is also applicable to other HCFCs such as 2,2-dichloro-1,1,1-trifluoroethane ("123") and 2-chloro-1,1,1,2-tetrafluoroethane ("124").

The inhibitor is present in an effective amount, typically from about 0.01 to about 2% by weight, based on the weight of the blowing agent(s), preferably 0.05 to 1%.

The compositions may also include a polyol or a fully formulated B-side formulation containing polyol, catalyst, surfactant, and, optionally, other additives. Typical polyols are, for example, Stepanol PS 2502A, an aromatic polyester polyol sold by the Stepan Company; Terate 203, an aromatic polyester polyol sold by Hercules, Inc.; Pluracol Polyol 975, a sucrose-based polyol sold by BASF; Poly-G 71-530, a polyether polyol sold by Olin; and Quadrol, an amine-based polyol supplied by BASF. Typical catalysts include Potassium HEX-CEM, a potassium octoate sold by Mooney Chemicals; Polycat 41, an N,N,N-tri(dimethylaminopropyl)cyclohexatriazine catalyst sold by Air Products; Polycat 8, an N,N-dimethylcyclohexylamine catalyst sold by Air Products; Dabco TMR-30, a 2,4,6-tri(dimethylaminomethyl)phenol supplied by Air Products; and Dabco K-15, a potassium 2-ethylhexoate in diethylene glycol supplied by Air Products. A typical surfactant is Dow Corning 193, a silicone polymer surfactant. A typical A-side component is Mondur E-489, an aromatic diisocyanate supplied by Mobay Chemical Co., or Lupranate M20S, a polymethylene-diisocyanate supplied by BASF.

The invention was illustrated by first preparing a polyurethane foam with 141b in the absence of inhibitor by stirring a formulation containing polyol (100 g of Stepanol PS 2502A), 141b (25.8 g), surfactant (1.51 g of Dow Corning 193), catalyst (2.82 g of Potassium HEX-CEM and 0.7 g of Polycat 41), and diisocyanate (127.2 g of Mondur E-489). The contents were poured into a box and the resulting foam was left to cool to room temperature. After curing the foam at 250° F for 20 hours, the cell gas was analyzed by crushing a sample and injecting the released gas mixture directly to a gas chromatograph. The gas was found to contain 2180 ppm of 1131a, whereas the 141b starting material contained only 10 ppm of 1131a. Other minor components in the cell gas totalled only about 440 ppm, similar to the levels found in the 141b starting material. When 0.6 weight % of 1,4-benzoquinone and DEHA were dissolved in 141b, foams prepared as aforesaid contained only 1095 ppm and 386 ppm of 1131a, respectively.

In another illustration, a polyurethane foam was prepared with 141b in the absence of inhibitor by stirring a B-side formulation containing polyol (60 g of Pluracol Polyol 975 and 40 g of Quadrol), 141b (30 g), surfactant (1.5 g of Dow Corning 193), and catalyst (2.5 g of Polycat 8) with an A-side comprised of diisocyanate (118.7 g of Lupranate M20S). The resulting foam was cured at 121 degrees Centigrade and analyzed as in the first illustration. The cell gas was found to contain 2313 ppm of 1131a. When 0.6 weight % of 2,6-di-t-butyl-benzoquinone was dissolved in the 141b, foam prepared as aforesaid contained only 1520 ppm of 1131a.

In a third test, polyisocyanurate premixes containing 141b (uninhibited and inhibited with 0.6 weight % DEHA) were aged at 130° degrees F. The premixes contained a polyol (100 g of Stepanol PS-2502A), 141 b (37 g), surfactant (3 g of Dow Corning 193), and catalyst (2.8 g of Dabco K-15 and 0.9 g of Dabco TMR-30). The uninhibited premix was found to contain 100 ppm of 1131a, while the premix containing DEHA contained only 70 ppm of 1131a.

Other compounds containing the hydroxyamine or quinone functionality should also be useful, such as hydroxyamines of the formula R1R2NOH where R1 and R2 are independently selected from hydrogen, methyl, isopropyl, t-butyl, and phenyl, and 1,4-benzoquinones where the backbone is substituted at the 2,3,5, and/or 6 positions with hydrogen, methyl, ethyl, isopropyl, t-butyl, and phenyl.

What is claimed is:

1. A composition comprising 1,1-dichloro-1-fluoroethane and an inhibitor selected from diethylhydroxylamine, 1,4-benzoquinone, and 2,6-di-t-butylbenzoquinone.

2. A composition as in claim 1 wherein the inhibitor is diethylhydroxylamine.

3. A composition containing a hydrochlorofluorocarbon blowing agent and an inhibitor selected from diethylhydroxylamine, 1,4-benzoquinone, and 2,6-di-t-butylbenzoquinone.

* * * * *